United States Patent [19]

Kozulic et al.

[11] Patent Number: 5,259,943
[45] Date of Patent: Nov. 9, 1993

[54] APPARATUS AND METHOD FOR SUBMERGED GEL ELECTROPHORESIS

[75] Inventors: Branko Kozulic; Urs Heimgartner, both of Zürich, Switzerland

[73] Assignee: Elchrom Ltd., Horgen, Switzerland

[21] Appl. No.: 909,831

[22] Filed: Jul. 7, 1992

[30] Foreign Application Priority Data

Nov. 9, 1990 [GB] United Kingdom ................ 9024428

[51] Int. Cl.$^5$ ............................................. B01D 61/00
[52] U.S. Cl. ................................................ 204/299 R
[58] Field of Search ..................................... 204/299 R

[56] References Cited

U.S. PATENT DOCUMENTS 4,588,491 5/1986 Kreisher et al. ................ 204/299 R Primary Examiner—John Niebling
Assistant Examiner—C. Delacroix-Muirheid
Attorney, Agent, or Firm—Walter C. Farley

[57] ABSTRACT

Electrophoresis apparatus for conducting electrophoresis in submerged gels, comprises a plurality of compartments including at least one gel compartment and at least one reservoir compartment; a plate as the bottom of a gel compartment, electrodes only in a gel compartment; the electrodes arranged in such a way that during operation the created electric field is confined essentially within a rectangular box, the said rectangular box defined on sides by side walls or barriers, on top by air and on bottom by the plate; means to circulate buffer; and barriers in a gel compartment mounted on the plate in front of buffer circulation openings.

24 Claims, 8 Drawing Sheets

APPARATUS AND METHOD FOR SUBMERGED GEL ELECTROPHORESIS

BACKGROUND OF THE INVENTION

Electrophoresis is a process for separation of charged species. It is based on the fact that various species migrate with different mobility in an electric field. Small species, like metal ions, as well as large species such as viruses have been separated by electrophoretic techniques. Nevertheless the technique is currently used mostly for separation of biological macromolecules, including proteins, nucleic acids and their derivatives. The process is usually carried out by forcing the molecules to migrate through an aqueous gel. The mobilities depend on structure of the gel, electric field and characteristics of ions themselves, including net surface charge, size and shape.

The gels used in electrophoresis fall into two broad categories. They may be composed of natural or synthetic polymers. Agarose is the most widely used natural material and polyacrylamide gels represent the most common synthetic matrix. The gels are employed in essentially two types of electrophoretic units: vertical and horizontal ones. Running the gels in the vertical format has some advantages. Since the gels are cast between two plates they are uniform, may be very thin and therefore the heat produced during the run can be dissipated easily, resulting in highly reproducible band patterns. On the other hand, it is more difficult to prepare vertical gels and they are prone to tearing during removal of the gel from the cassette. In contrast to vertical units, handling of gels is easy in horizontal electrophoresis units. During a run the gel rests flat on a platform. A contact between the electrodes and the gel may be established directly or by means of wicks. Alternatively, in submerged gel electrophoresis the gel is immersed in buffer which serves as a conductive medium between electrodes and the gel. This format is the simplest and is widely used for analysis of nucleic acids. Agarose gels are almost exclusively used for submerged gel electrophoresis of nucleic acids.

An apparatus for submerged gel electrophoresis usually includes a base and a pair of opposing tanks. Each tank has a buffer containment zone and an electrode. A gel is placed on said base between the tanks and is in communication with the buffer containment zones. The layer of buffer is usually 2-4 mm high above the gel and up to 10 cm high in the tanks. The electrodes are situated typically near the bottom of the tanks parallel to the gel.

Modified versions of the above described apparatus, such as the one described by Turre et al (U.S. Pat. No. 4,415,418) are also known. A similar unit but suitable for bidimensional electrophoresis has been also disclosed (Serwer, U.S. Pat. No. 4,693,804). In these apparatus the electric field density is higher in the gel compartment than in the buffer tanks.

The resolution of nucleic acids in agarose gels using the above described submerged gel electrophoresis units is satisfactory, as it is widely known. When electrophoretic runs need to be performed for a prolonged time it is advantageous to recirculate and cool the buffer. Some submerged gel electrophoresis units, essentially constructed as described above, have a port in each tank. Tubing is then connected to the ports and a pump is used to circulate the buffer. The buffer in the tubing is electrically charged and therefore circulation of buffer in this manner represents a potential safety hazard. In addition, the evenness of buffer flow over the gel surface is not addressed in these units.

An apparatus in which the buffer circulates in another way is Hoefer model HE 100 B (Hoefer Scientific Instruments, San Francisco). Although electrically charged, the buffer circulates inside the unit through a spiral containing a magnetic stirring bar in the center. The spiral is positioned between two buffer tanks. Rotation of the stirring bar by means of a magnetic stirrer on which the electrophoresis unit rests draws the buffer from one tank into the other. However, the electric field density also in this unit is higher in the gel compartment than in the buffer tanks.

Separation of large DNA molecules in agarose gels can be greatly improved by pulsed field electrophoresis (Cantor and Schwartz, U.S. Pat. No. 4,473,452). Other units for pulsed field electrophoresis have been also described (for example, Chu et al (1986) Science, 232, 1582). In some of these units the side and end walls do not define the electric field as in the units described above. The electric field is instead closed by a specific electrode arrangement.

As already noted, polyacrylamide and agarose gels have been the matrices mostly used for electrophoretic analysis of biomolecules. A new synthetic matrix has been introduced for analysis of proteins and nucleic acids by Kozulic et al (U.S. patent application Ser. No. 328,123, Analytical Biochemistry 163 (1987) 506-512 and Analytical Biochemistry 170 (1988) 478-484). It is based on an acrylic monomer, N-acryloyl-tris(hydroxymethyl)aminomethane (NAT). The poly(NAT) gels were found to be more porous than polyacrylamide gels but less porous than agarose gels. Therefore they offer advantages for separation of large proteins and those nucleic acids whose size is out of the optimal separation range of agarose and polyacrylamide gels. In the cited references, the superior properties of the poly(NAT) gels for analysis of DNA were demonstrated after running the gels in a vertical format. However, we have surprisingly found that in the standard submerged electrophoresis units the resolution of DNA in the poly(NAT) gels was never so good as in the vertical system. The major difference was observed in the lower half of the gel, where the bands became much more diffuse. Moreover, the DNA fragments in the middle lanes migrated further than the corresponding fragments in the outer lanes. This phenomenon is known as the smiling effect. Further, very often DNA bands were straight only in the middle but the edges were bent upwards.

The occurrences described above were less pronounced with agarose gels run under identical conditions. Agarose gels used for DNA analysis usually contain from 0.5 to 2% of polymer dry weight. On the contrary, the poly(NAT) gels we have used contained from 6 to 12% of polymer dry weight. It is expected therefore that poly(NAT) gels give a higher resistance to migration of buffer ions through the gel. Accordingly the heat produced during electrophoresis, known as Joule heat, is expectedly higher in poly(NAT) than in agarose gels. There are many examples in prior art demonstrating that controlling Joule heat is essential for achievement of optimal electrophoretic separations. It is also known that the electric field should be as uniform as possible.

In the standard submerged gel electrophoresis apparatus, there is no control over the Joule heat and the electric field is not uniform, as schematically depicted in FIG. 1a. The field density is higher in the gel region 102 than in the buffer tanks 101. In addition, the electric field lines 105 are curved in the gel region. The curvature depends mostly on distance between the electrodes 106, 106' and gel region, position of the electrodes and level of buffer 104 above the gel 103. The curvature can be reduced and the uniformity of electric field improved by placing the electrodes 107, 107' in the same plane to the gel, as shown in FIG. 1b. However, the electric field lines are still curved, especially if the level of buffer is high above the gel. Other positions of the pair of electrodes relative to the gel are possible, but the electric field uniformity cannot be substantially improved. As an element of this invention, it was realized that two pairs of electrodes 108, 108', one positioned above the other, will produce a substantially more uniform electric field in the region between the electrodes, as shown in FIG. 1c. While the uniformity of electric field is very important, it will give the expected improvement in electrophoretic resolution only with an apparatus in which additional requirements are fulfilled. Most important of these additional requirements are control of the Joule heat and prevention of buffer ion depletion in the gel region, that is accumulation of cations close to cathode and anions close to anode. These requirements are fulfilled in the apparatus of the present invention, as will be realized from the explanations hereinunder.

OBJECTIVES OF THE INVENTION

It is the principal objective of the present invention to provide an improved apparatus for conducting submerged gel electrophoresis of charged species in aqueous gels, especially in poly(NAT) gels.

It is another objective of the present invention to provide an improved method for submerged gel electrophoresis of DNA in poly(NAT) gels.

SUMMARY OF THE INVENTION

In the practice of the principles of the present invention it is possible to resolve DNA fragments better than in the standard way. The improved resolution is particularly beneficial in detecting DNA restriction fragment length polymorphism and in analysis of DNA amplification products.

In a first preferred embodiment, the apparatus of the present invention includes an upper buffer compartment as the gel compartment, a lower buffer compartment as the reservoir compartment and a horizontal plate between the two compartments as the bottom of the gel compartment. According to a feature of the invention, the bulk of buffer is in the lower compartment but the electrodes are in the upper compartment. This allows formation of a more uniform electric field in the gel compartment without creating too high current. The aforesaid horizontal plate could be also a heat exchanger connected to an external heater/cooler. Buffer circulates between the two compartments through openings in the horizontal plate. Two separated openings are positioned on each side of the horizontal plate between the side walls and long vertical barriers in the upper compartment. The barriers direct the flow of buffer and delimit the electric field in the upper compartment. A pump is mounted to the bottom of the lower compartment, and as an additional advantageous feature of the embodiment, the buffer between the inlet and outlet of the pump is substantially uncharged. The flow of buffer in the gel compartment is guided by a pair of dams, perpendicular to the long barriers, close to each end of the horizontal plate. According to another feature of the invention two pairs of electrodes, as shown in FIG. 1c, are employed, creating a substantially more uniform electric field than in the standard units. The electrodes are positioned parallel to the long barriers and the flow of buffer is essentially perpendicular to the electric field lines.

In a second preferred embodiment of the invention, the electrodes are positioned perpendicular to the long barriers. They are close to the inner side of the dams which regulate the flow of buffer in the upper compartment. The flow of buffer is essentially parallel to the electric field lines.

In a third preferred embodiment of the invention, there are two openings in the horizontal plate, one in the middle of each end side close to the end wall. There is a vertical barrier in front of each opening. The barriers are shorter than the end walls. The flow of buffer in the upper compartment is regulated by two dams positioned parallel to the vertical barriers. The electrodes are parallel to the side walls and the flow of buffer is essentially perpendicular to the electric field lines.

In a fourth preferred embodiment of the invention, the upper compartment is partitioned into two separate chambers. The horizontal plate has four pairs of openings, two for each chamber. The electrodes in the two chambers are independent and the two electric fields are separated. Buffer circulates from one buffer reservoir into two gel compartments.

DESCRIPTION OF THE DRAWINGS

The above and other objectives, features and advantages of the present invention will become more readily apparent from the following descriptions, reference being made to the accompanying drawing in which.

DETAILED DESCRIPTION OF THE PREFERRED EMBODIMENTS

The following descriptions contain by way of example various definite dimensions. These relate to certain laboratory models made and tested. The dimensions are clearly illustrative and are not to be construed in any limitative manner.

Figure 13:
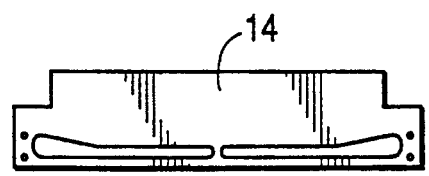
FIG. 13 is a view of a modified dam for the embodiment of FIGS. 2 to 7.

All apparatus of the present invention are made of a non-conductive material. Referring to FIGS. 2, 3, 4, 5 and 6, the apparatus of a preferred embodiment is basically composed of side plates 1, 1', end plates 2, 2', bottom plate 3 of the reservoir compartment, horizontal plate 4 forming the bottom of the gel compartment and the electrode assembly (FIG. 3). The horizontal plate 4 defines an upper and a lower buffer compartment. In the upper compartment on each side of the horizontal plate there are two openings, 5, 6 and 5', 6', separated by small vertical barriers 7 and 7'. The openings connect buffer of the upper and lower compartments. Long vertical barriers 8 and 8', are mounted in front of the openings on each side of the horizontal plate, contiguous to the small barriers 7 and 7'. The long barriers are somewhat shorter than the length of the adjacent sides of the horizontal plate. In the lower buffer compartment, there is a dam 9 dividing the lower compartment into two rooms. The dam contains openings in the corners and in the middle and it is positioned between the two openings on each side of the horizontal plate. A pump 10 is mounted to the bottom of the lower compartment. Inlet 11 of the pump is on one side and outlet 12 is on the other side of the dam 9. The pump draws buffer from openings 5 and 5' and pushes it through openings 6 and 6'. As indicated by the arrows, in the upper compartment the buffer flows between the long barriers and side walls on both sides. The two streams turn and combine when they come to the end wall 2. The flow is then directed by dams 13 and 14. In the preferred embodiment dam 13 has a long half-ellipsoidal opening and dam 14 a long slot. To increase its mechanical stability, the slot in dam 14 may have a bar in the middle. The slot is somewhat above the horizontal plate. The slots in dam 14 instead of having parallel upper and lower sides may be modified to be tapered towards the center, as shown in FIG. 13, for better control of the flow profile of the buffer. The half-ellipsoidal opening in dam 13 is in its midpoint 1–5 mm higher than the slot in modified dam 14. The level of buffer is kept 1–5 mm above the half-ellipsoidal opening. After passing the dams 13 and 14 the buffer flows in the central part of the horizontal plate and proceeds through similar dams 13' and 14'. When it comes to end wall 2', the stream splits and goes between the long barriers and side walls back into the lower compartment through openings 5, 5'. The buffer circulates also between the two rooms in the lower compartment through openings in dam 9. The size of openings in this dam and the size of openings 5, 5' and 6, 6' in the horizontal plate determine mostly the flow rate in the upper compartment. When the openings in dam 9 are small the flow rate in the upper compartment increases and it decreases when the openings are large.

The electric field is created by electrodes 15 and 15' made of a conductive material such as for example platinum wire. Two pairs of electrodes spaced apart 11 cm horizontally and 7 mm vertically, are connected to plugs 16 and 16' which are mounted on plug cubes. Preferentially the wires pass through dams 13 and 13' and their ends are not more than 1 cm away from end walls 2 and 2'. It has been observed that the electric field is disturbed when the electrodes span only the distance between dams 14 and 14'. That is manifested by distortion of DNA bands in the lanes nearest to dam 14 or 14'. The electrodes may be alternatively mounted onto the surface of barriers 8 and 8', but in that case gaseous electrolysis products in the form of bubbles tend to become larger and remain longer on electrodes. Since the bubbles may disturb the electric field it is better to stretch the electrodes between the dams at least 1 mm apart from the barriers 8 and 8'. When the lower electrode is also at least 1 mm above the horizontal plate, the formed bubbles are small and they readily detach from the wires. Disturbance of the electric field is accordingly minimized. Mounting the electrodes on the dams has an additional advantage. By bridging the dams with two long bars 17 and 17', a removable electrode assembly is formed. The assembly fits snugly between barriers 8, 8' and end walls 2, 2'. Movement of the electrode assembly in the upward direction is prevented by four blocking pieces 19 (only two are shown). After inserting them through holes in the end walls, rods from the blocking pieces 19 come just above the plug cubes and cubes 18, 18'.

Figure 5:
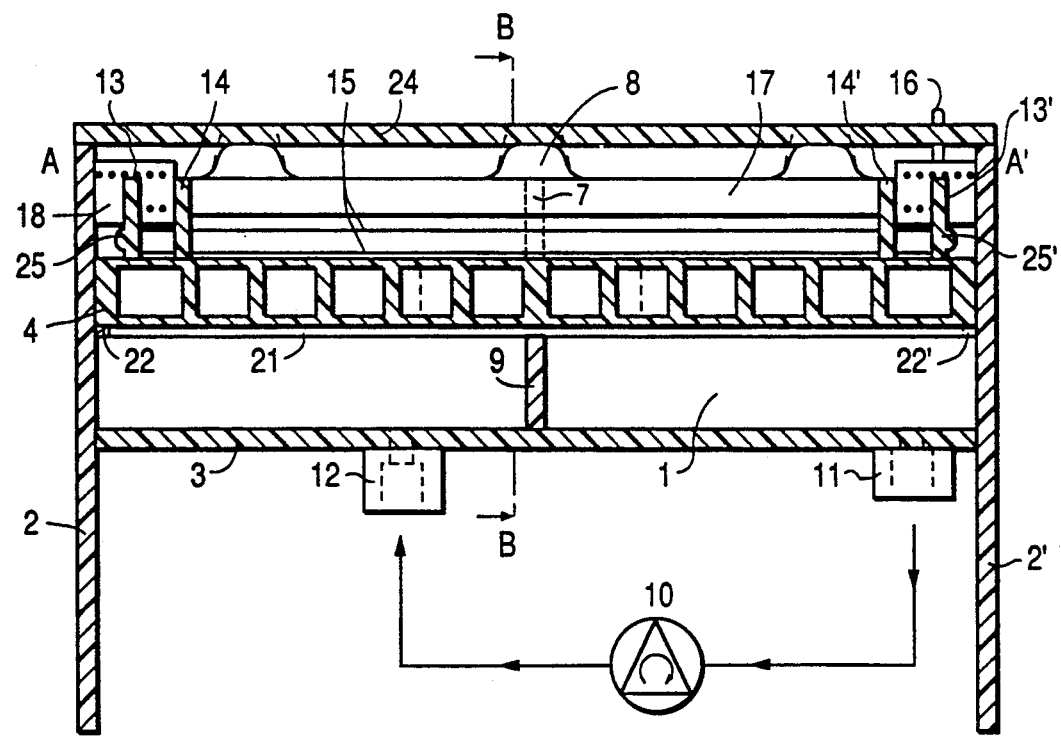
FIG. 5 is a cross sectional view of the electrophoresis apparatus taken along line 5—5, of FIG. 4.
Figure 6:
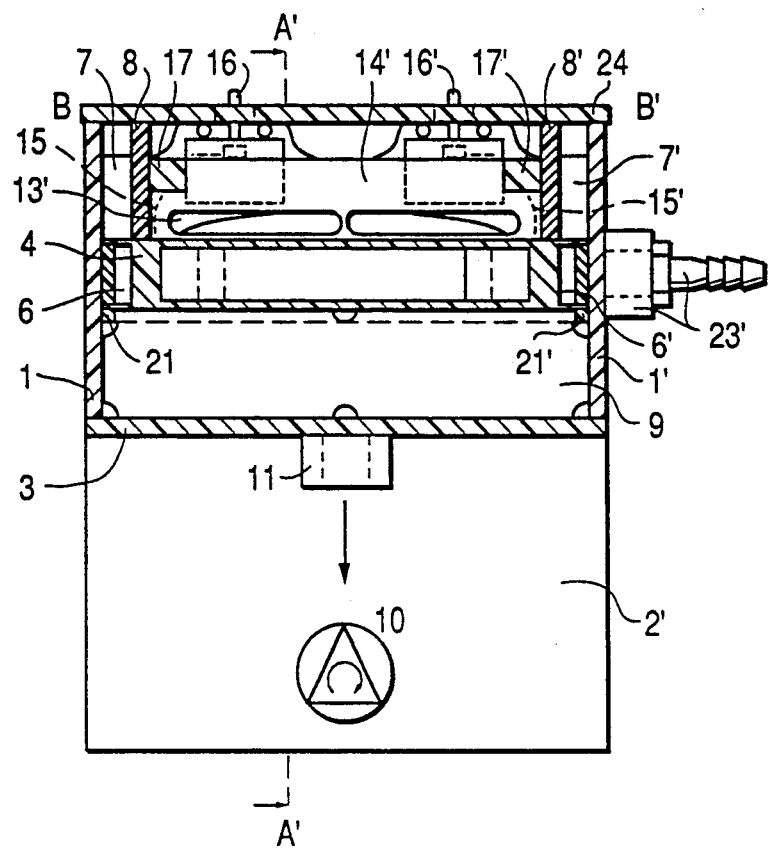
FIG. 6 is a cross sectional view of the electrophoresis apparatus taken along line 6—6 of FIG. 4.

The barriers 8 and 8' have two purposes. They initially direct the flow of buffer when it enters the upper compartment. Second, the barriers delimit the electric field substantially into the upper compartment. Since the buffer is pumped in and out of the lower compartment, as indicated in FIG. 5, the buffer in the pump is not induced by the electric field. The apparatus of the present invention has therefore the important advantage that it avoids pumping of strongly charged electrophoresis buffer.

To run a gel, it is placed between the electrodes in central part of the horizontal plate. Since there is a flow of buffer, the gel should be secured to prevent its floating with the stream. A convenient way to fix the gel is by means of a frame 20, made of an electrically nonconductive material. The frame has handle 20' and two long slots of dimensions similar to the slot of dam 14. It is advantageous to cast the gel on a support film somewhat larger than the gel itself. The frame 20 is then placed to rest on two edges of the gel support. Another role of the frame 20 is to improve evenness of the buffer flow in the upper compartment. It is clear that the frame 20 may vary in width in dependence on the gel size. Also it is apparent that more than one frame 20 may be placed in the gel compartment.

Figure 7:
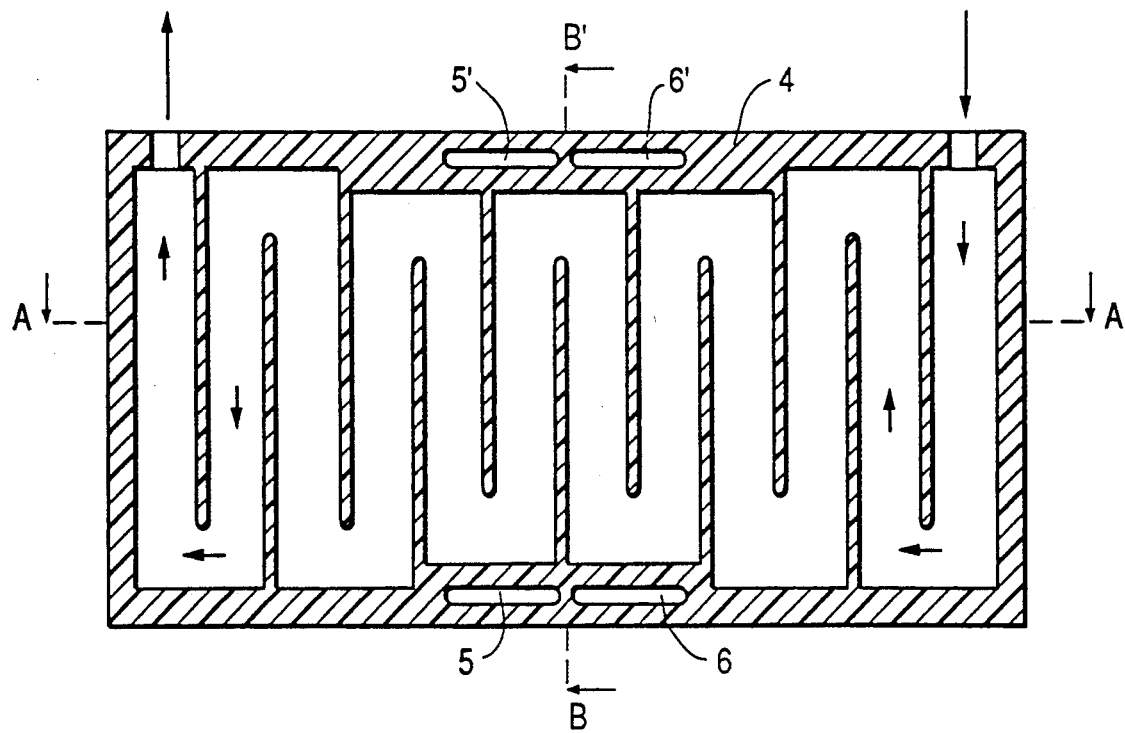
FIG. 7 is a cross sectional view of the horizontal plate.

As noted above, heat is produced during electrophoresis. The horizontal plate 4 in this embodiment serves to control the heat. To facilitate horizontal alignment of the plate 4 during construction of the apparatus, strips 21, 21' are fixed on the side plates 1,1' and strips 22, 22' are fixed onto the end plates 2, 2'. A cross section of the horizontal plate is shown in FIG. 7. A coolant circulates through the serpentine inside the plate, indicated by small arrows, and in and out as indicated by big arrows. The inlet and outlet holes in the plate 4 are aligned with holes of the same size in side wall 1' and with larger holes of tube connections 23, 23'. The heat is exchanged through the top and through the bottom of the horizontal plate. On the top, usually a larger part of the surface is covered with a gel, so that the heat exchange between buffer and the horizontal plate occurs predominantly through the bottom of the plate in the lower compartment. Heat equilibration is facilitated by buffer mixing resulting from pumping the buffer through dam 9 from one into the other room of the lower compartment. On the other hand, heat from the gel dissipates partially into the horizontal plate under the gel and partially into the buffer flowing over the gel. When desirable buffer temperature is in the range from 15° to 30° C., the top and bottom of the horizontal plate may be made of a 1-2 mm thick common plastic material. However, if desirable buffer temperature is below 15° or above 30° C., it is better to use another electrically nonconductive material which is superior as a heat conductor.

Cover 24 should be in place on top of the apparatus before starting the run since it forms a shield against accidental electrical contact by the experimenter. The cover has two holes large enough to allow connection of jacks to plugs 16 and 16'.

In the preferred embodiment two wires are taken for electrodes mainly for two reasons. First, the electric field created by two wires is more uniform than the electric field created by one wire. Second, the resulting electric current produced by two pairs of electrodes is not too high. It was observed that when two wires were used instead of one, the amperage increased approximately by a factor of two. Thus, when the buffer was 30 mM Tris-acetate, 0.75 mM $Na_2EDTA$ at 70 V the amperage was about 70 mA with one electrode and about 140 mA with two electrodes. Thus it is clear that current at a given voltage depends on the number of wires. The use of three or more wires improves the uniformity of electric field but the amperage also increases. A high amperage is deleterious because more heat is produced and because composition of the electrophoresis buffer changes faster due mostly to electrolysis. Therefore, in the present invention two wires for an anode and two wires for a cathode are regarded as optimal. However, in those applications requiring even more uniform electric fields or very low voltages it may be advantageous to use more than two wires or a conductive strip as an anode and as a cathode.

The volume of buffer in the gel compartment is such that it just covers the upper wire. The current at a given voltage then increases with the vertical distance between the two wires. Therefore, to keep current low this distance should not be too large. On the other hand, uniformity of electric field is not improved if the vertical distance between the wires is too small. As a feature of the present invention, it is found that the vertical distance from 3 to 10 mm is satisfactory. The optimal distance may be out of this range if anode and cathode are substantially closer or substantially more apart than in the described embodiment. The current depends also on thickness of wires. In choice of the thickness important considerations are also mechanical stability and cost. Suitable are from 0.1 to 0.5 mm thick wires made of platinum.

In order to maintain the two electrodes vertically equidistant over the whole length, in a preferred embodiment a single 0.2 mm thick platinum wire passes through holes in dams 13, 14, 13' and 14'. In addition, two pieces of silicon tubing 25 and 25' are inserted between the wire and dams 13 and 13' so that the wire presses the tubing against the dam. This means of keeping the wire stretched is preferred due to its simplicity.

In a first preferred embodiment, the horizontal distance between the electrodes is 11 cm. It is apparent that the electrodes may be positioned at a longer or at a shorter distance. The gap of 11 cm is chosen since a gel length of about 9 cm is sufficient for many application. In the present invention poly(NAT) gels 92 mm long are used. They are placed in the center of the area between the two electrodes. Accordingly, the gel ends are about 9 mm distant from the electrodes. This distance is substantially shorter than the distance between the gel and electrodes in the standard submerged gel electrophoresis apparatus. Therefore, the apparatus of this invention has the additional advantage that it is more compact and so the useful gel area is proportionally larger than in the standard unit.

During electrophoresis the gel is kept in place with frame 20. The gel is positioned inside the frame which rests on the protruding gel support film. The frame 20 accommodates a gel that is longer than wide. It is also possible to have a gel equally long and wide or wider than longer. The corresponding frames will therefore vary in their dimensions. When a gel is of size matching the frame 20, then three gels can be placed and run at the same time in one electrophoresis unit of a first preferred embodiment. Two frames 20 are sufficient to fix three gels when the support film protrudes by half thickness of the vertical side of frame 20.

The volume of buffer in the gel compartment of a first preferred embodiment is from about 2 to about 5 fold larger that the maximal gel volume, gel thickness being 3 to 6 mm. While this buffer volume may be sufficient, and therefore another buffer compartment unnecessary, for running agarose gels at a low voltage for a short time, a larger buffer volume is better for running synthetic gels due mostly to three reasons. First, a synthetic gel usually contains millimolar concentrations of the polymerization catalysts which migrate out of the gel during electrophoresis. The composition of buffer therefore changes gradually and the larger the buffer volume the smaller will be the relative change in composition. Second, a synthetic gel always contains a small quantity of unpolymerized monomers which diffuse out of the gel during the run. Many vinyl monomers react with some functional groups present in biomolecules in a concentration dependent way. Hence a larger buffer volume is better because the unpolymerized monomers will be more diluted. Third, during electrophoresis Joule heat is produced. A larger buffer volume is again better since it has a higher heat capacity and therefore temperature fluctuations during the run are smaller. In a preferred embodiment, a suitable buffer volume is from 8 to 40 fold larger than the total gel volume, but even a higher buffer quantity may be desirable in some applications. The apparatus of this invention has therefore the important advantage that it allows usage of a large amount of buffer.

Figure 1A:
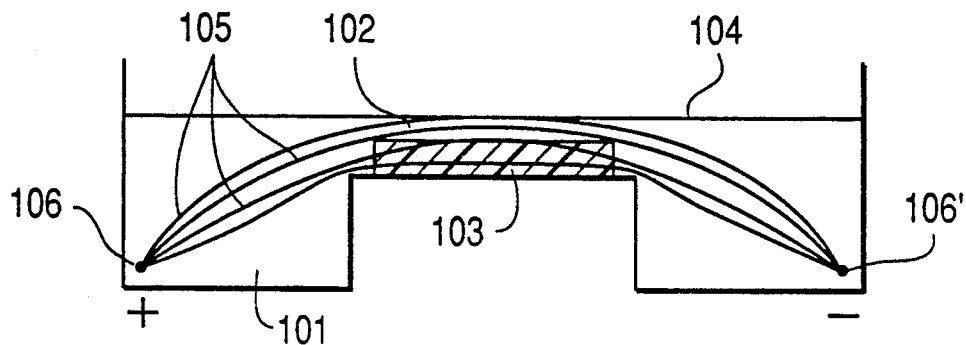
FIG. 1a is an outline of electric field in the standard submerged electrophoresis apparatus.
Figure 1B:
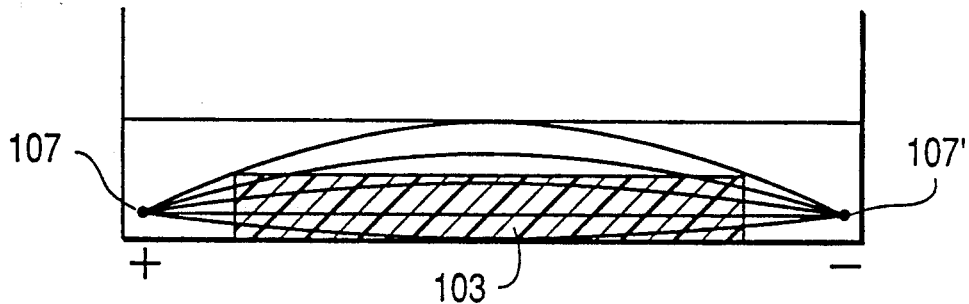
FIG. 1b is an outline of electric field created by two electrodes positioned in plane to the gel.
Figure 1C:
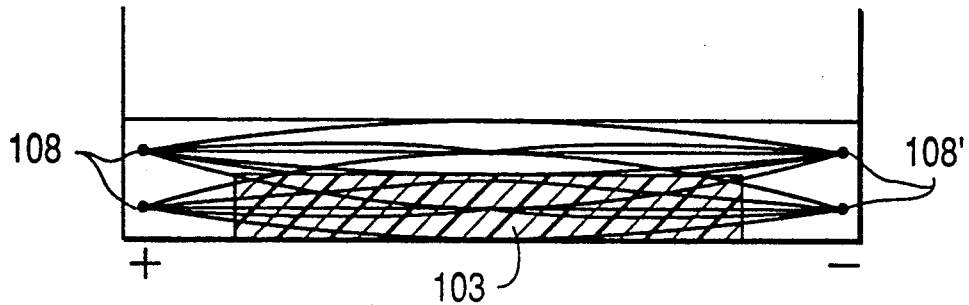
FIG. 1c is an outline of electric field created by two pairs of electrodes.
Figure 2:
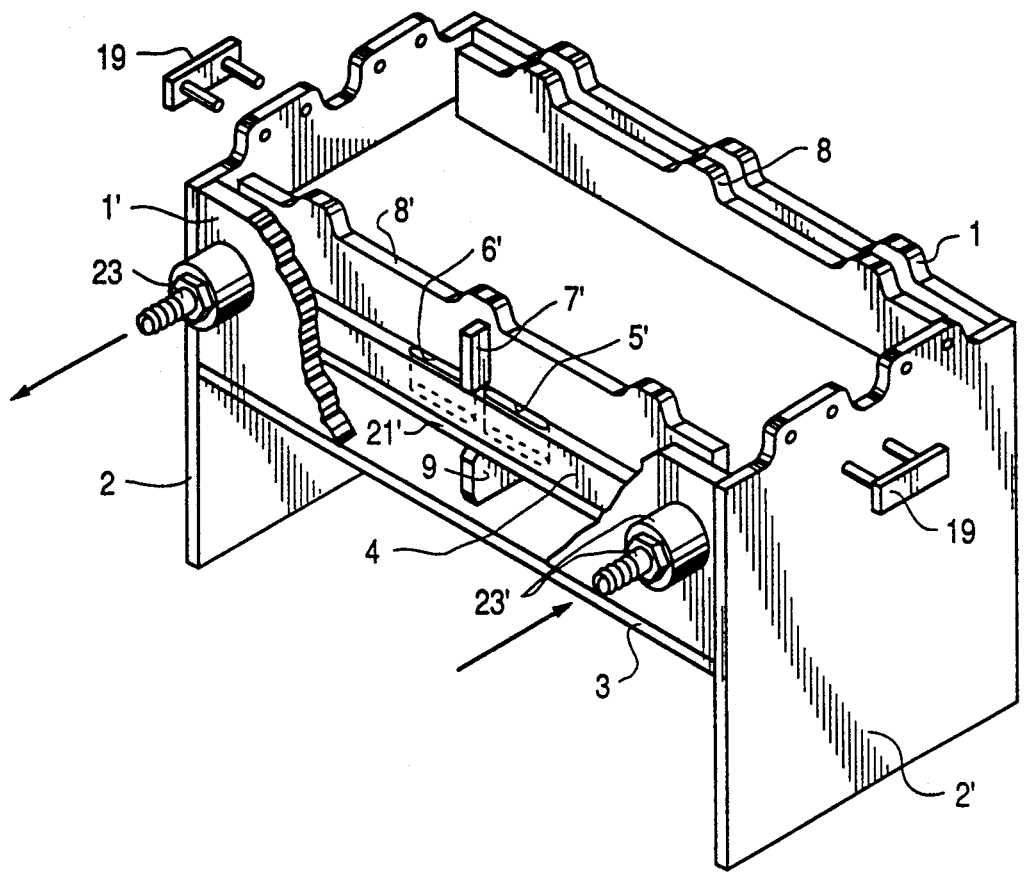
FIG. 2 is a perspective view of the base of an electrophoresis apparatus according to this invention.
Figure 3:
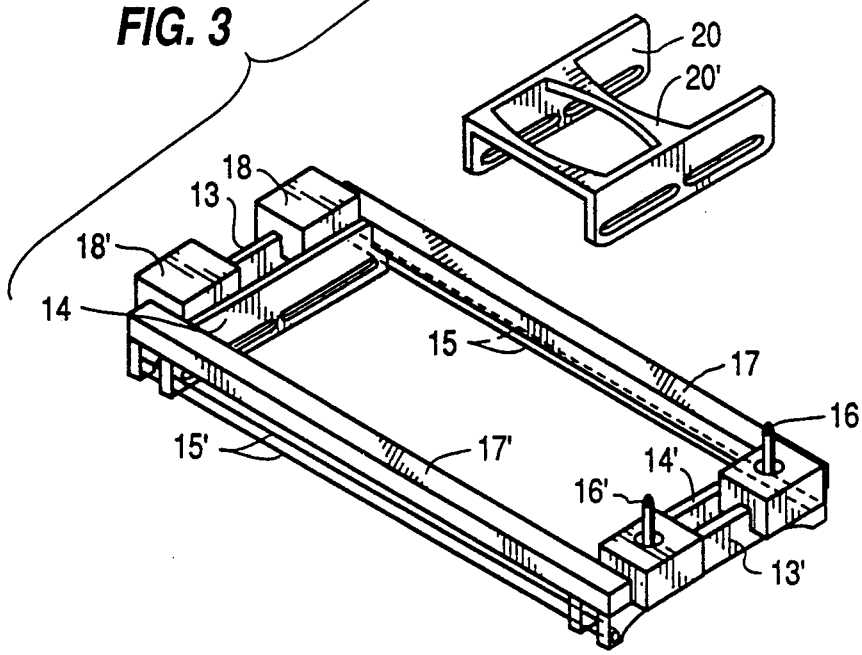
FIG. 3 is a perspective view of an electrode assembly with long electrodes and of a frame.
Figure 4:
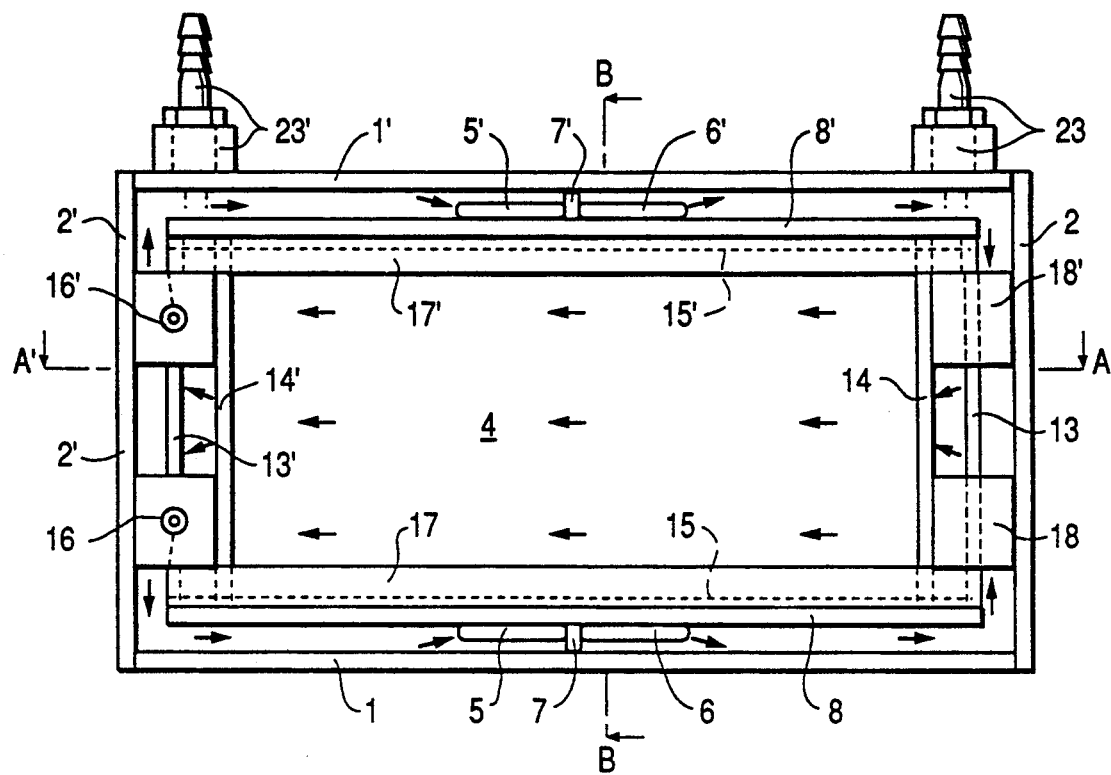
FIG. 4 is a diagrammatic plan view of the electrophoresis apparatus shown in FIG. 2, with the electrode assembly of FIG. 3 in place.
Figure 8:
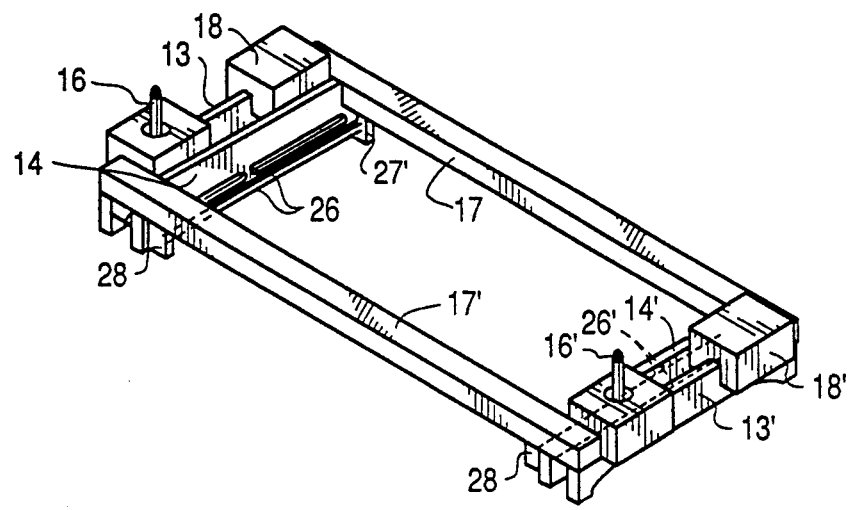
FIG. 8 is a perspective view of an electrode assembly with short electrodes.

In second preferred embodiment, the electrode assembly shown in FIG. 8 is inserted into the upper compartment of the basic unit shown in FIG. 2. The electrodes 26 and 26' are mounted onto pieces 27, 27' and 28, 28', fixed perpendicularly to dams 14 and 14' and kept stretched in the same manner as described in the first preferred embodiment. The electrodes 26 and 26' are shorter than electrodes 15 and 15' but they are more distant. Accordingly, a longer gel may be run in the area between these two electrodes. The novel apparatus of the present invention has the further advantage that it allows running of gels substantially different in length. That capability comes from the possibility to interchange the electrode assembly. However, it is clearly possible to fix the electrodes permanently in the apparatus of this invention. That would eliminate the risk of damage during electrode assembly exchange but at the same time it would also limit the size of gels that can be run.

In second preferred embodiment, the flow of buffer is essentially parallel to the electric field lines whereas in a first preferred embodiment the flow is essentially perpendicular to the electric field lines. Angles of 90° and 180° are chosen because they are most convenient. It is apparent that the buffer may flow at yet another angle with respect to the electric field lines.

Figure 9:
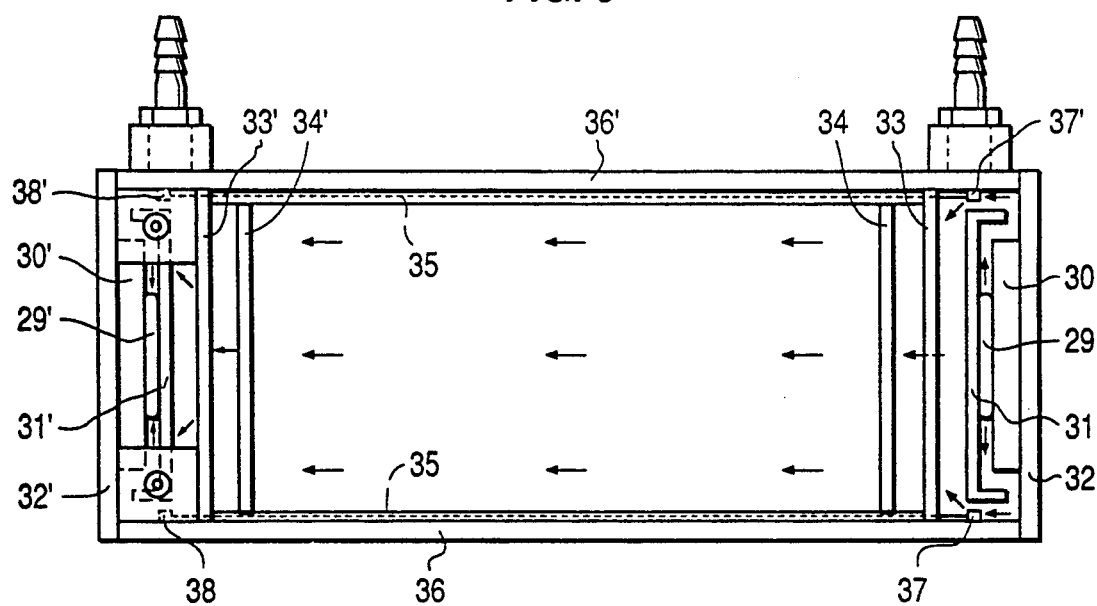
FIG. 9 is a plan view of an electrophoretic apparatus with buffer recirculation openings on ends of the horizontal plate.

In a third preferred embodiment shown from the top in FIG. 9, there are two openings 29 and 29' in the horizontal plate. There are vertical barriers 30, 31, and 30', 31' in front, on sides and behind the openings. The buffer flows through opening 29 between barriers 30 and 31 and the end wall 32. Then it turns and passes under dams 33 and 34, which comprise openings of the same shape as the openings of dams 13 and 14 of a first preferred embodiment. After passing the central area, the stream passes dams 34' and 33' and enters opening 29' by moving between end wall 32' and barriers 30' and 31'. Other features of the horizontal plate as well as of the lower compartment are substantially the same as those in a first preferred embodiment.

The electrodes 35 and 35' are parallel to the side walls 36 and 36' and the flow of buffer is essentially perpendicular to the electric field lines. A suitable electric field is achieved when the electrodes span the distance between the electrode pieces 37, 37' and 38, 38'. The buffer level comes above these pieces. When the electrodes are shorter, DNA bands are distorted in the lanes nearest to the barriers 34 and 34'.

Figure 10:
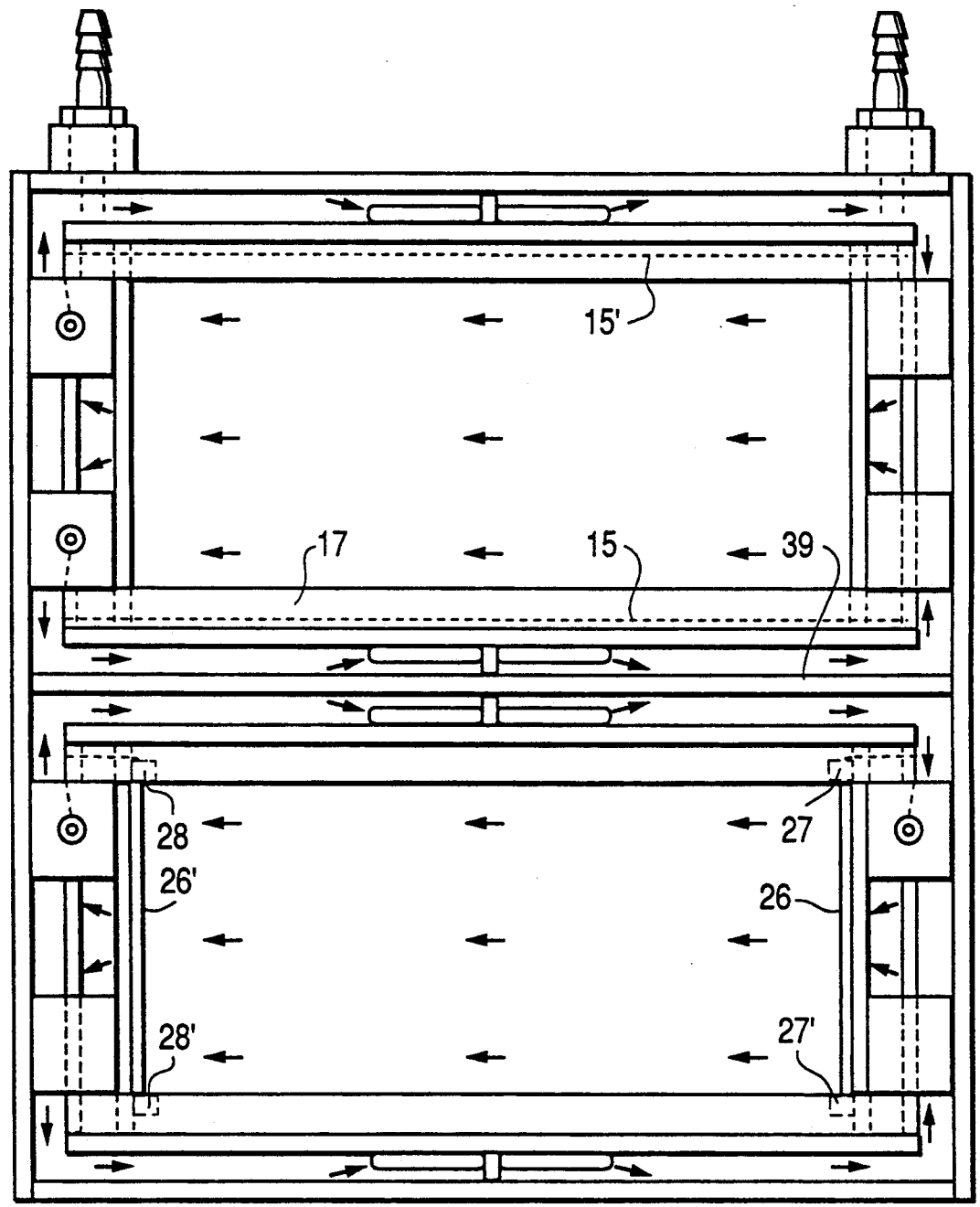
FIG. 10 is a plan view of an electrophoresis apparatus with two separate electrophoresis chambers in the upper compartment.

In a fourth preferred embodiment shown from the top in FIG. 10, the upper compartment is divided in two separate chambers. The horizontal plate has four pairs of openings, two for each chamber. The electrodes in the two chambers are independent and the electric field in one chamber is separated from the electric field in the other chamber. Buffer circulates from one lower compartment into two upper chambers. It is evident that the upper compartment of this apparatus consists essentially of one upper compartment of a first embodiment and one upper compartment of second embodiment. The important difference is the long vertical barrier 39 which separates the two chambers. A single horizontal plate is shared by both chambers.

The apparatus of the fourth preferred embodiment is advantageous mainly because a gel in one chamber can be run under different conditions, at different voltage for instance, from the gel in second chamber at the same time. It is apparent that many modifications, within the scope of this invention, are feasible on the apparatus of the fourth preferred embodiment. Two such modifications will be referred to. According to the first one, the upper chambers may comprise the buffer recirculation openings and barriers shown in FIG. 9. According to the second one, the upper compartment may include more than two, for instance four, separate chambers to enable running of four gels each under different conditions but at the same time.

Figure 11:
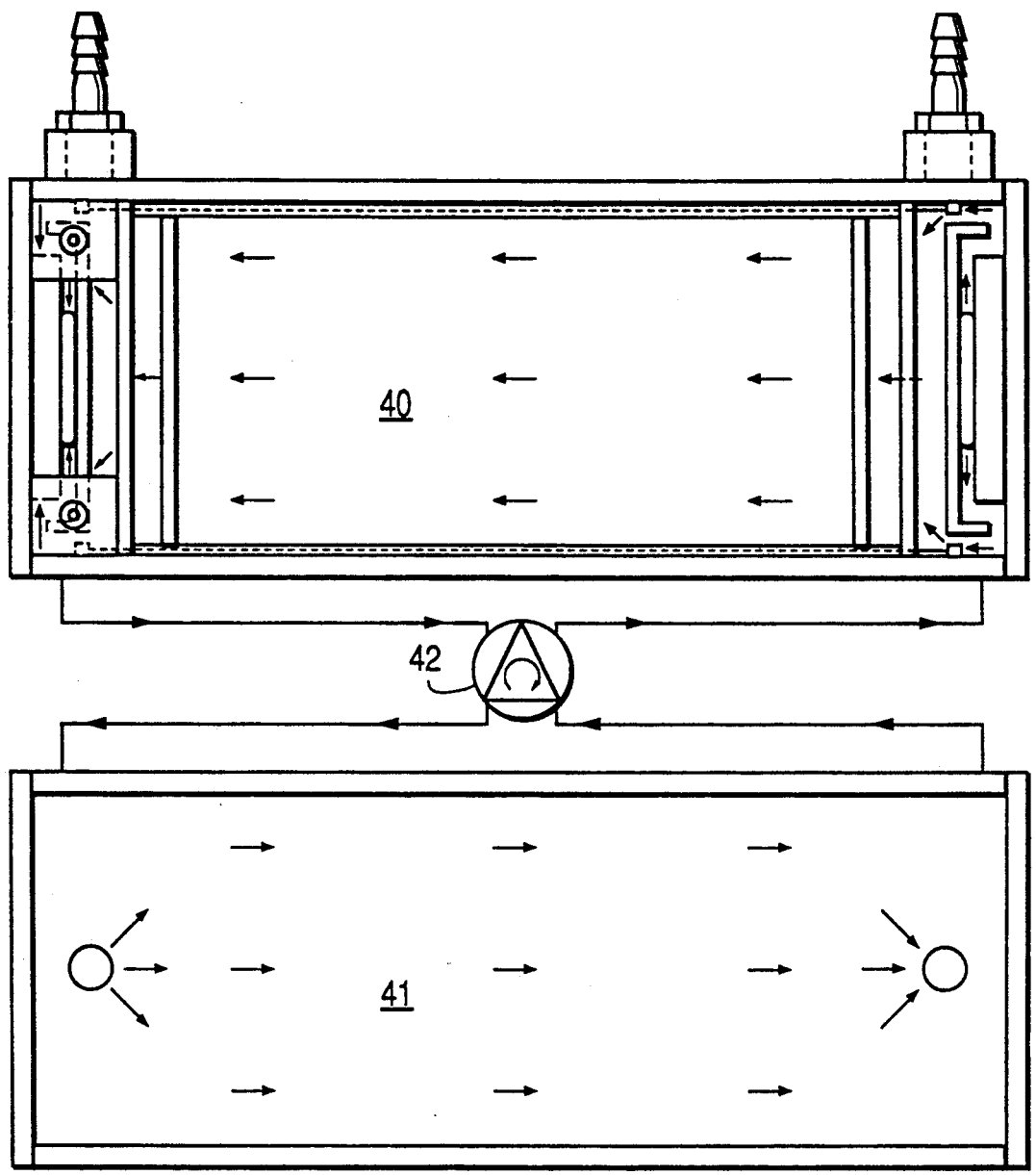
FIG. 11 is a schematic plan view of an electrophoresis apparatus with a gel compartment and a reservoir compartment placed side by side.

In the above description of the preferred embodiments a few possible modifications were mentioned. It will be apparent to those skilled in the art that many additional changes, resulting in other embodiments within the scope of this invention, can be made. The brief descriptions of some of these possibilities hereinunder, not intended as limitations unless otherwise specifically indicated herein, are illustrative. Thus, in another embodiment, outlined in FIG. 11, it is possible to place a gel compartment 40 and a reservoir compartment 41 side by side. Pump 42 is used to circulate buffer. When the pump uses tubings of identical diameter the level of buffer in the resevoir compartment can be different from the level of buffer in the gel compartment. Alternatively the buffer can be pumped only into one opening of the gel compartment and then flow through a tubing in the reservoir compartment. The level of buffer is then essentially the same in the compartments. In this embodiment buffer recirculation openings are also positioned in the horizontal plate. In yet another embodiment, buffer circulation openings may be placed into side or end walls or at other locations in the horizontal plate. In a further embodiment, the horizontal plate and/or the buffer may be cooled by a Peltier element instead by a circulating coolant. In a further example, dams in the electrode compartment may comprise openings of shapes different from those of dams 13 and 14. In yet a further case, an electrode may include instead of two, one, three or more wires or a strip comprising a conductive material.

EXAMPLE

Figure 12:
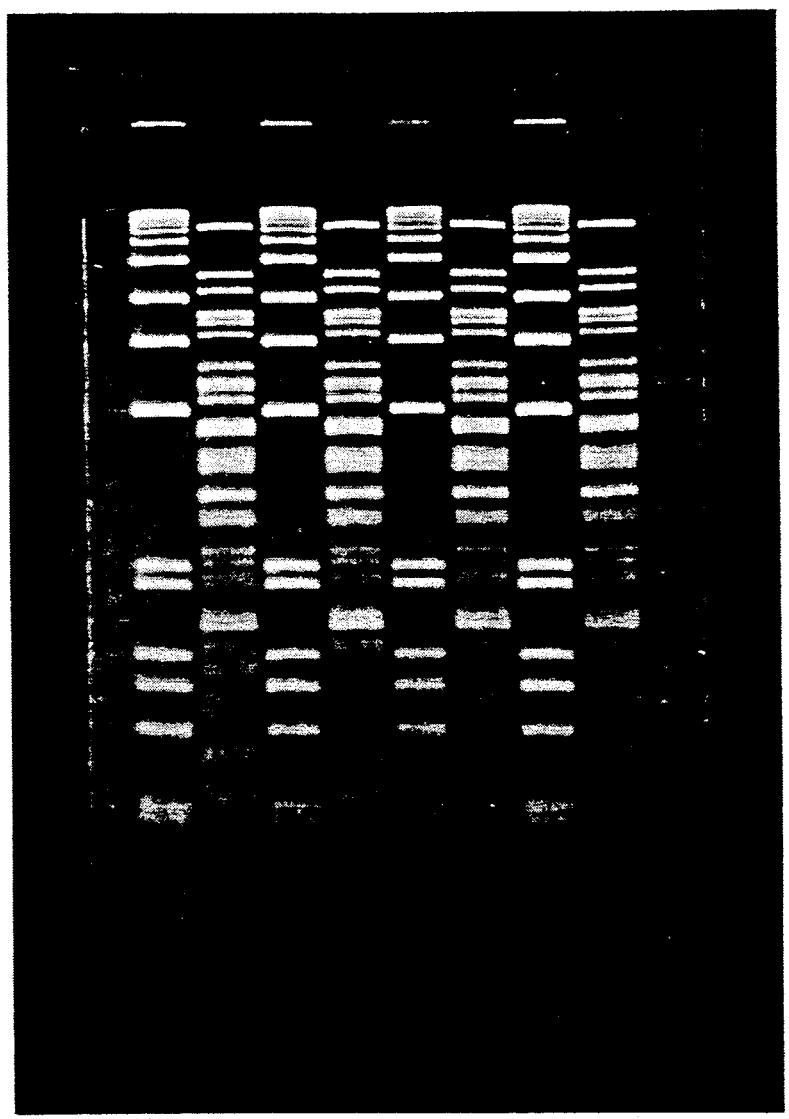
FIG. 12 is a DNA band pattern in a 6% poly(NAT) gel after submerged gel electrophoresis in the apparatus according to this invention.

According to a method of the present invention, DNA fragments of different size are electrophoresed in a 6% poly(NAT-Bis) gel in the apparatus of a first preferred embodiment. Electrophoresis buffer is 30 mM Tris-acetate pH 8.0, containing 0.75 mM $Na_2EDTA$. About 1700 ml of buffer is poured in the unit. The gel is 92 mm long, 62 mm wide and 3 mm thick. The plastic support film protrudes 2 mm on each side of the gel. The gel is placed on top of the horizontal plate and no air bubbles are allowed to remain entrapped between the support film and the horizontal plate. The gel is kept in place by means of the frame 20. Additional buffer is added until the level of buffer comes about 2 mm above the upper platinum wire. The DNA samples are diluted with electrophoresis buffer containing 40% sucrose and 0.005% bromphenol blue. Two different DNA samples are used. One is a commercially available mixture of well defined DNA fragments (1 kb ladder, Bethesda Research Laboratories) and the other is Mva I restriction digest of bacteriophage lambda DNA. Four 5 μl portion of each sample are applied to the gel. The sample wells are 5.5 mm long, 1.5 mm wide and 2.5 mm deep. After loading of samples, the cover is closed and voltage set to 77 V. At this voltage the current corresponds to about 170 mA. The electric field strength is 7 V/cm in the area between the two electrodes. As judged from migration of the bromphenol blue tracking dye, the DNA fragments enter the gel in about 4 minutes. At this time, circulation of buffer is started by switching on the pump. During electrophoresis the buffer temperature is 25° C. when the circulating coolant, coming from an LKB model 2219 Multi Temp II Thermostatic Circulator, has a temperature of 24.5° C. After two hours and about 20 minutes, the tracking dye reaches the bottom of the gel. Power is then disconnected and the gel incubated for one hour in 100 ml of distilled water containing 100 μg of ethidium bromide. In order to dilute the excess of ethidium bromide, the gel is soaked overnight in one liter of distilled water in the dark. Subsequently the gel is photographed under a UV light. From the DNA pattern shown in FIG. 12 it is evident that there is no smiling effect. In addition, the bands are straight over the whole band width. Finally, the resolution in the 200-2000 base pair range is excellent and particularly significant is resolution of the 506 and 516 base pairs fragments.

The present invention has been described in considerable detail, and it will be apparent to those skilled in the art that modifications and changes, some of which are referred to hereinabove, may be made in the procedure and in the apparatus itself without departing from the concept and scope of the invention as described in the following claims.

What we claim is:

1. An electrophoresis apparatus for conducting electrophoresis in submerged gels comprising the combination of
   a plurality of compartments including a gel compartment and a reservoir compartment for holding buffer solution;
   a plate forming a bottom of said gel compartment;
   a plurality of walls attached to said plate forming sides and ends of said gel compartment;
   electrodes within said gel compartment,
   said electrodes being arranged to create a more linear an electric field confined essentially within said gel compartment as defined by said side walls, said end walls, said plate and on top by air;
   means for circulating said buffer solution;
   means defining buffer circulation openings between said reservoir compartment and said gel compartment; and
   barriers in said gel compartment mounted on said plate spaced from selected ones of said walls and in front of said buffer circulation openings so that buffer solution can flow between said walls and said barriers.

2. An apparatus according to claim 1 wherein said electrodes comprise two parallel wires forming an anode and a cathode, and means for mounting said wires with a vertical spacing from about 2 to about 20 mm.

3. An apparatus according to claim 2 wherein said means for mounting is removably positioned in said gel compartment.

4. An apparatus according to claim 2 wherein said plate includes means for stabilizing temperature during electrophoresis.

5. An apparatus according to claim 1 and comprising at least two gel compartments.

6. An apparatus according to claim 1 and comprising means for keeping the level of buffer solution substantially constant in said gel compartment.

7. An apparatus according to claim 6 wherein said means for circulating said buffer solution includes a pump.

8. An apparatus according to claim 1 wherein said circulation openings are in said walls to provide a flow passage between said gel compartment and at least one of said reservoir compartments.

9. An apparatus according to claim 1 and wherein said circulation openings are in said plate to provide a flow passage between said gel compartment and said reservoir compartment.

10. An apparatus according to claim 9 wherein said openings include two separated buffer solution circulation openings on each side of said plate.

11. An apparatus according to claim 10 and including two vertical barriers on said plate, one barrier positioned adjacent each said opening such that said opening is between said barrier and a wall of said gel compartment.

12. An apparatus according to claim 9 wherein said openings include an opening at each end of said plate.

13. An apparatus according to claim 12 and including two vertical barriers on said plate, one barrier positioned adjacent each said opening such that said opening is between said barrier and a wall of said gel compartment.

14. An apparatus according to claim 1 wherein said means for circulating includes a pump and inlet and outlet fittings connected to said pump and to a reservoir compartment; said reservoir compartment further including a dam between said inlet and outlet fittings, said dam having a plurality of openings therethrough.

15. An apparatus according to claim 1 wherein flow of buffer solution in said gel compartment is directed by two types of dams positioned perpendicular to the flow of buffer solution, one type of dam containing a semi-ellipsoidal opening and the other containing an elongated slot.

16. An apparatus according to claim 15 and including at least two dams with a semi-ellipsoidal opening and at least two dams with an elongated slot.

17. An apparatus according to claim 16 wherein said gel compartment includes two pairs of dams, the dams of each pair of dams being spaced apart by a distance of from 1 cm to 4 cm and each including one dam with a semi-ellipsoidal opening closest to an end wall of said gel compartment and being spaced from said end wall of said compartment by a distance of from 1 to 3 cm.

18. An apparatus according to claim 17 wherein said electrodes extend parallel with said side walls of said gel compartment.

19. An apparatus according to claim 17 wherein said electrodes extend parallel with said end walls of said gel compartment.

20. An apparatus according to claim 1 wherein said electrodes comprise two parallel wires forming an anode and a cathode, and means for mounting said wires with a vertical spacing from about 2 to about 20 mm, said means for mounting being removably positioned between said end walls and vertical barriers adjacent said end walls.

21. An apparatus according to claim 20 wherein said electrodes extend along said side walls of said gel compartment.

22. An apparatus according to claim 20 wherein said electrodes extend along said end walls of said gel compartment.

23. An apparatus according to claim 1 wherein said buffer circulation openings are positioned so that said buffer solution in said means for circulating is substantially free of electrical charge from said field created by said electrodes.

24. An electrophoresis apparatus for conducting electrophoresis in submerged gels comprising the combination of
   a plurality of compartments including a gel compartment and a reservoir compartment for holding buffer solution;
   a plate forming a bottom of said gel compartment;

a plurality of walls attached to said plate forming sides and ends of said gel compartment;

barrier walls in said gel compartment mounted on said plate spaced from selected ones of said walls and in front of said buffer circulation openings so that buffer solution can flow between said walls and said barrier walls;

electrodes within said gel compartment, said electrodes being arranged to create a more linear electric field confined essentially within said gel compartment as defined by said side walls, said end walls, said barrier walls, said plate and on top by air;

means for circulating said buffer solution; and means defining buffer circulation openings between said reservoir compartment and said gel compartment.

* * * * *